US009008774B2

(12) United States Patent
Pei et al.

(10) Patent No.: US 9,008,774 B2
(45) Date of Patent: Apr. 14, 2015

(54) CAPTURE THRESHOLD AND LEAD CONDITION ANALYSIS

(71) Applicant: Pacesetter, Inc., Sylmar, CA (US)

(72) Inventors: Xing Pei, Thousand Oaks, CA (US); Robert E. Smith, Jr., Bradbury, CA (US); Paul A. Levine, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/929,694

(22) Filed: Jun. 27, 2013

(65) Prior Publication Data

US 2013/0289645 A1 Oct. 31, 2013

Related U.S. Application Data

(62) Division of application No. 12/496,539, filed on Jul. 1, 2009, now Pat. No. 8,498,706, which is a division of application No. 10/987,731, filed on Nov. 12, 2004, now Pat. No. 7,574,259.

(51) Int. Cl.
*A61N 1/372* (2006.01)
*A61N 1/37* (2006.01)
*A61N 1/05* (2006.01)
*A61N 1/368* (2006.01)

(52) U.S. Cl.
CPC ............... *A61N 1/371* (2013.01); *A61N 1/056* (2013.01); *A61N 1/368* (2013.01); *A61N 1/372* (2013.01)

(58) Field of Classification Search
CPC ....... A61N 1/371; A61N 1/056; A61N 1/368; A61N 1/372

USPC ...................................... 607/27–28
See application file for complete search history.

(56) References Cited

U.S. PATENT DOCUMENTS

| 4,140,131 A | 2/1979 | Dutcher et al. |
| 4,686,988 A | 8/1987 | Sholder |
| 4,708,142 A | 11/1987 | DeCote, Jr. |
| 4,712,555 A | 12/1987 | Thornander et al. |
| 4,729,376 A | 3/1988 | DeCote, Jr. |
| 4,788,980 A | 12/1988 | Mann et al. |
| 4,940,052 A | 7/1990 | Mann et al. |

(Continued)

FOREIGN PATENT DOCUMENTS

| EP | 0338364 B1 | 7/1994 |
| EP | 0338363 B1 | 3/1995 |

(Continued)

OTHER PUBLICATIONS

Binner, Ludwig et al., "Autocapture Enhancements: Unipolar and Bipolar Lead Compatibility and Bipolar Pacing Capability on Bipolar Leads," PACE. 2003;26(Pt.. II):221-224.

(Continued)

*Primary Examiner* — Amanda Patton

(57) ABSTRACT

An exemplary method includes performing a capture threshold assessment using a bipolar electrode configuration, deciding if capture occurred for a maximum energy value of the capture threshold assessment and, if capture did not occur, then performing a lead impedance test for the lead associated with the bipolar electrode configuration. Such a test may aim to detect an insulation defect and/or a conductor defect. Other exemplary methods, devices, systems, etc., are also disclosed.

7 Claims, 12 Drawing Sheets

(56) References Cited

U.S. PATENT DOCUMENTS

| | | |
|---|---|---|
| 4,944,298 A | 7/1990 | Sholder |
| 4,969,467 A | 11/1990 | Callaghan et al. |
| 5,003,975 A | 4/1991 | Hafelfinger et al. |
| 5,350,410 A | 9/1994 | Kleks et al. |
| 5,466,254 A | 11/1995 | Helland |
| 5,476,483 A | 12/1995 | Bornzin et al. |
| 5,476,485 A | 12/1995 | Weinberg et al. |
| 5,814,088 A | 9/1998 | Paul et al. |
| 5,855,594 A | 1/1999 | Olive et al. |
| 6,327,498 B1 | 12/2001 | Kroll |
| 6,430,441 B1 | 8/2002 | Levine |
| 6,546,288 B1 * | 4/2003 | Levine ............................. 607/28 |
| 7,031,773 B1 | 4/2006 | Levine et al. |
| 7,308,310 B1 | 12/2007 | Levine et al. |
| 7,738,959 B2 * | 6/2010 | Manrodt et al. ................. 607/28 |
| 2002/0147477 A1 | 10/2002 | Pons et al. |

FOREIGN PATENT DOCUMENTS

| | | |
|---|---|---|
| EP | 0770408 B1 | 3/2004 |
| WO | 0020071 | 4/2000 |

OTHER PUBLICATIONS

Clarke, Malcolm et al., "Automatic Adjustment of Pacemaker Stimulation Output Correlated with Continuously Monitored Capture Thresholds: A Multicenter Study," PACE. 1998;21:1567-1575.

Dorwarth, Uwe MD et al., "Transvenous Defibrillation Leads: High Incidence of Failure during Long-Term Follow-Up," J Cardiovasc Electrophysiol. 2003;14:38-43.

Restriction Requirement, mailed Jul. 25, 2012: Parent U.S. Appl. No. 12/496,539.

NonFinal Office Action, mailed Aug. 31, 2012: Parent U.S. Appl. No. 12/496,539.

Notice of Allowance, mailed May 22, 2013: Parent U.S. Appl. No. 12/496,539.

* cited by examiner

EXEMPLARY BIPOLAR LEAD FAILURES

|     | Lead Conductor 1 | | Lead Conductor 2 | |
| --- | --- | --- | --- | --- |
|     | Insulation | Conductor | Insulation | Conductor |
| C1  | 0 | 0 | 0 | 0 |
| C2  | 1 | 0 | 0 | 0 |
| C3  | 1 | 1 | 0 | 0 |
| C4  | 1 | 1 | 1 | 0 |
| C5  | 1 | 1 | 1 | 1 |
| C6  | 0 | 1 | 0 | 0 |
| C7  | 0 | 1 | 1 | 0 |
| C8  | 1 | 1 | 0 | 1 |
| C9  | 0 | 0 | 1 | 0 |
| C10 | 1 | 0 | 1 | 0 |
| C11 | 1 | 0 | 1 | 1 |
| C12 | 1 | 0 | 0 | 1 |
| C13 | 0 | 1 | 0 | 1 |
| C14 | 0 | 0 | 0 | 1 |
| C15 | 0 | 0 | 1 | 1 |
| C16 | 0 | 1 | 1 | 1 |

*Fig. 6*

CAPTURE THRESHOLD AND LEAD CONDITION ANALYSIS

CROSS REFERENCE TO RELATED APPLICATIONS

This application is a division of U.S. patent application Ser. No. 12/496,539, filed Jul. 1, 2009, which is a division of U.S. patent application Ser. No. 10/987,731, filed Nov. 12, 2004, now U.S. Pat. No. 7,574,259.

TECHNICAL FIELD

Subject matter presented herein generally relates to cardiac pacing, cardiac shock, detection, sensing and/or stimulation therapies. Various exemplary mechanisms concern condition of leads used for pacing, shock, detection, sensing and/or stimulation.

BACKGROUND

Various studies indicate that an implanted lead may fail for one or more reasons. For example, a study by Dorwarth et al., "Transvenous defibrillation leads: high incidence of failure during long-term follow-up", *J Cardiovasc Electrophysiol.*, 14(1):38-43 (2003), found that a majority of lead-related sensing failures were associated with insulation defects that occurred late after ICD placement (6.0+/−1.8 years after implant). Dorwarth et al. recognized that "automated device control features with patient alert function integrated into new devices may contribute to early detection of lead failure". Thus, a need exists for techniques to detect lead failure.

To date such techniques typically rely heavily on impedance measurement. For example, excessive lead impedance may indicate loss of a connection due to a conductor fracture and low lead impedance may indicate a short circuit or alternative conduction path due to an insulation failure. To date, impedance techniques are typically implemented by a care provider during follow-up or perhaps on a programmed, periodic basis (e.g., time schedule). Such techniques may not uncover lead issues in a timely manner. As described herein, various exemplary mechanisms are presented that can improve timeliness of detection and/or improve timeliness of adjustments to therapy in response to a lead issue. Other advantages are also discussed herein.

SUMMARY

An exemplary method includes performing a capture threshold assessment using a bipolar electrode configuration, deciding if capture occurred for a maximum energy value of the capture threshold assessment and, if capture did not occur, then performing a lead impedance test for the lead associated with the bipolar electrode configuration. Such a test may aim to detect an insulation defect and/or a conductor defect. Other exemplary methods, devices, systems, etc., are also disclosed.

In general, the various devices, systems and/or methods described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

FIG. 6 is a table of various lead conductor and insulation conditions for a two conductor lead.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate and/or shock tissue.

Figure 1:
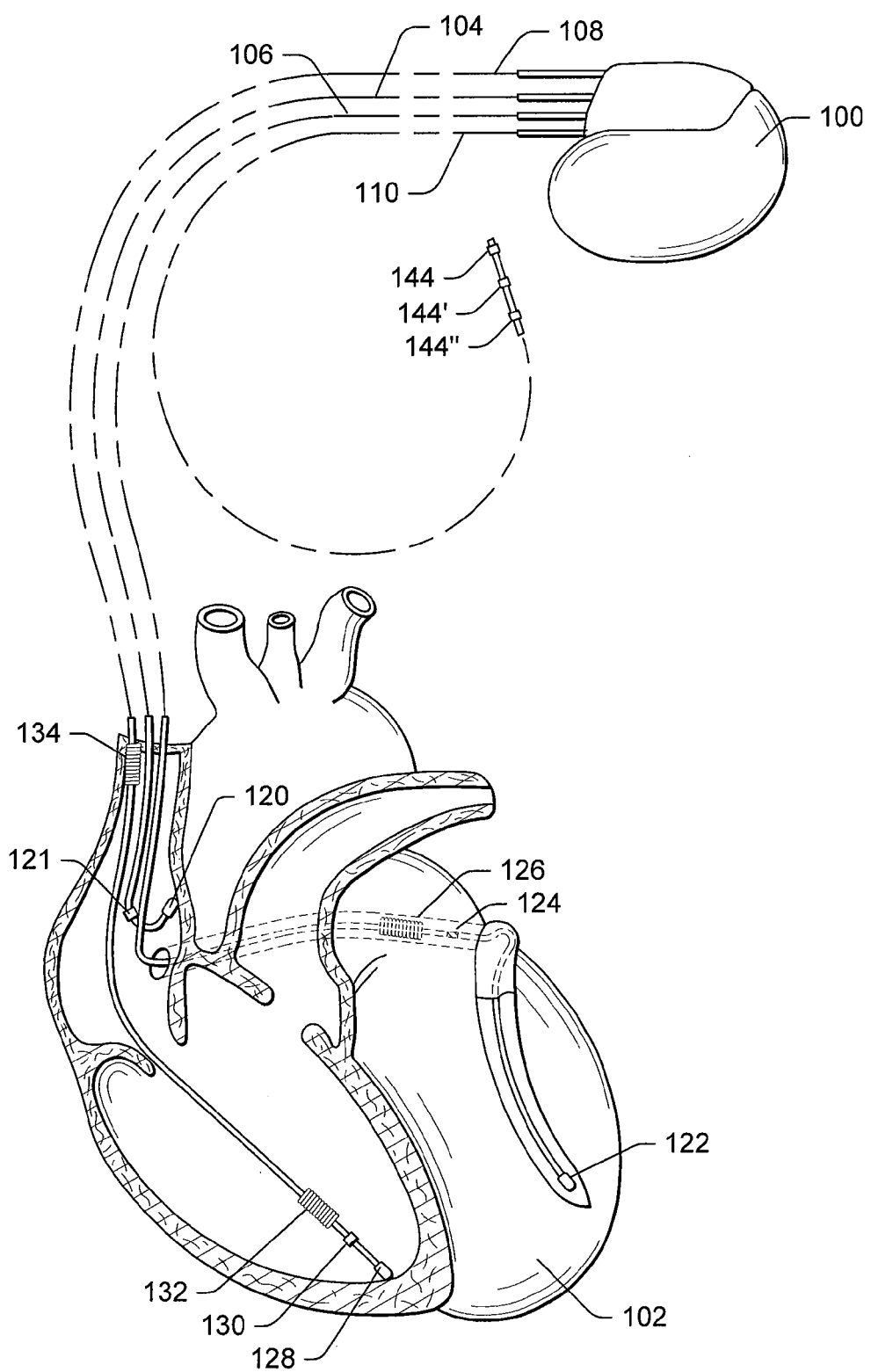
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
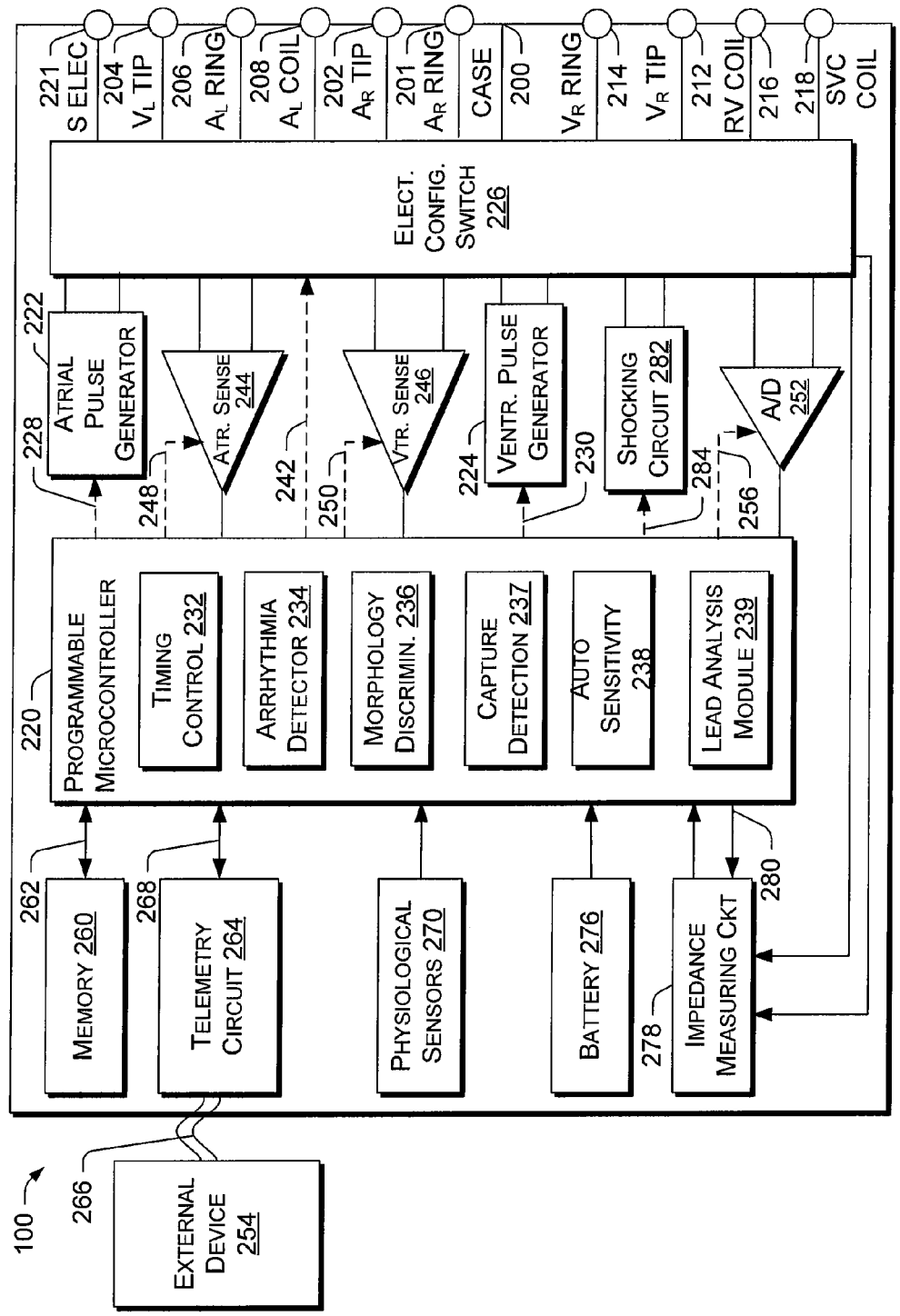
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, an auto sensitivity module 238, a lead analysis module 239 and optionally an orthostatic compensator and a minute ventilation (MV) response module, the latter two are not shown in FIG. 2. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation.

The lead analysis module 239 may perform a variety of tasks related to, for example, lead condition. This component can be utilized by the stimulation device 100 in determining therapy in response to condition of insulation and/or a conductor associated with an electrode. The lead analysis module 239 may be implemented in hardware as part of the microcontroller 220, or as software/firmware instructions programmed into the device and executed on the microcontroller 220 during certain modes of operation. The lead analysis module 239 may optionally implement various exemplary methods described herein. The lead analysis module 239 may interact with the capture detection module 237 and optionally other modules, such as the sensitivity module 238.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between events (e.g., P-waves, R-waves, and depolarization signals associated with fibrillation which are sometimes referred to as "F-waves" or "Fib-waves") detected via sensed information may be also classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, and an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. A magnet or magnetic field may also be capable of triggering storage of data, such as IEGM data.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds, cardiac condition (e.g., heart failure indications such as pulmonary edema, etc.); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Figure 3:
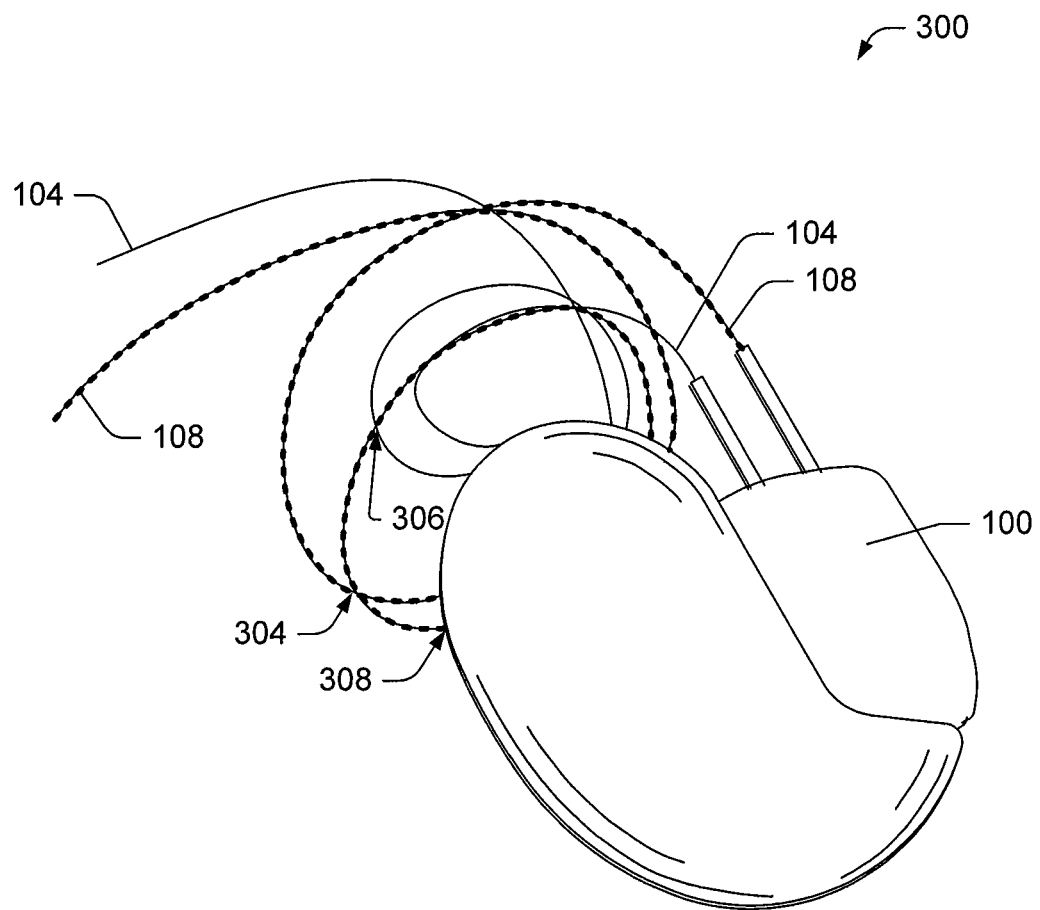
FIG. 3 is a diagram of an exemplary implantable device that includes two leads that are looped and in proximity (e.g., possible contact) with the case of the implantable device.

FIG. 3 shows an exemplary implant arrangement 300 that includes an exemplary device 100 and two leads 104, 108. Implanted cardiac pacing, detection, sensing and/or shock devices are typically positioned subcutaneously in a left pectoral pocket. Implanted devices for deep brain stimulation may also be positioned in a pectoral or other pocket. In either instance, actual lead length typically exceeds needed lead length. As such, upon implantation, one or more leads may be looped and positioned proximate to or in the device's pocket. X-ray images of implanted cardiac stimulation devices appear in various journals and serve to illustrate such looping.

In FIG. 3, the leads 104, 108 each loop twice before extending to the left side of the figure and represent a typical implant arrangement. As the leads 104 and 108 loop, they may self-contact 304, contact each other 306 and/or contact the device 308. In other instances, one or more of the leads may contact bone or other hard tissue. All of these forms of contact may cause, typically over an extended time, lead insulation defects or failures. Various exemplary methods, devices and/or systems aim to help detect such defects and/or failures.

An example of a conventional configuration for unipolar right ventricular pacing may include use of a cathodic right ventricular tip electrode on a right ventricular lead connected at a connector (e.g., the connector 212) and an anodic case electrode at a case connector (e.g., the connector 200). Such a configuration may have a corresponding resistance, $R_{Conv}(V_{R\text{-}Uni})$, between the two electrodes. As discussed herein, and elsewhere, a change in such a resistance may indicate a change in a lead, electrode, tissue or other issue.

In another example, a conventional bipolar right ventricular pacing configuration may include use of a cathodic right ventricular tip electrode on a right ventricular lead connected at a connector (e.g., the connector 212) and an anodic right ventricular ring electrode on a right ventricular lead connected at a connector (e.g., the connector 214). Such a configuration may have a corresponding resistance, $R_{Conv}(V_{R\text{-}BiP})$, between the two electrodes. As discussed herein, and elsewhere, a change in such a resistance may indicate the existence of a lead, electrode, tissue or other issue.

In yet another example, a conventional unipolar shock configuration may include use of a cathodic right ventricular coil electrode on a right ventricular lead connected to a connector (e.g., the connector 216) and an anodic case electrode at a case connector (e.g., the connector 200). Such a configuration may have a corresponding resistance, $R_{Conv}(V_{R\text{-}Shock})$, between the two electrodes. As discussed herein, and elsewhere, a change in such a resistance may indicate a change in a lead, electrode, tissue or other issue (e.g., existence of an issue).

Various lead problems may affect battery condition. For example, in a first scenario where an electrode impedance exceeds 2500Ω, current drain from an associated and typical cardiac stimulation device is minimal and less than 10 µA. While such a scenario is not desirable, the battery life would be quite long, for example, equal to or greater than 10 years. Thus, a scenario that involves a fractured wire, a loose connection, and/or no connection may be associated with a low current drain and high impedance; noting that various scenarios may also result in ineffective stimuli, inappropriate stimuli, faulty sensing, etc.

In a second scenario representative of normal operation, an electrode impedance of approximately 500Ω (e.g., a pacing electrode), an average current drain of approximate 21 µA and a battery life of about 5 years may be expected. In general, normal impedance ranges from about 300Ω to about 1500Ω for cardiac pacing electrodes. In a third scenario where electrode impedance is less than about 200Ω, an average current drain of about 63 µA and a shortened battery life of about 2 years may result. Such a scenario is undesirable for at least several reasons. First, the increase in current drain can shorten battery life dramatically and, second, an insulation break typically exposes at least a portion of a lead conductor and thus creates secondary current paths. Of course actual current drain may also depend on pacing voltage, therapy, etc.

With respect to low energy stimuli and/or sensing, insulation defects such as those associated with the third scenario may cause inappropriate stimulation and/or inappropriate sensing. Inappropriate stimulation may fail to stimulate target tissue and/or cause an increase in stimulation energy accelerating battery depletion while inappropriate sensing may cause an implanted device to implement inappropriate therapy and compete with native complexes or withhold delivery of therapy resulting in asystole and/or report incorrect data. With respect to higher energy stimulation or shock, an insulation defect or failure may have catastrophic consequences. For example, if the lead 108 of FIG. 3 has an insulation failure adjacent to the case of the device 100, a high energy pulse delivered via the lead 108 may cause arcing between the lead conductor to the case of the device 100 and permanently damage the ICD while failing to deliver sufficient energy to the heart to defibrillate it. In general, if friction between a lead and a case causes an insulation defect, then a high likelihood exists for contact or a short circuit between a conductor of the lead and the case.

Figure 4:
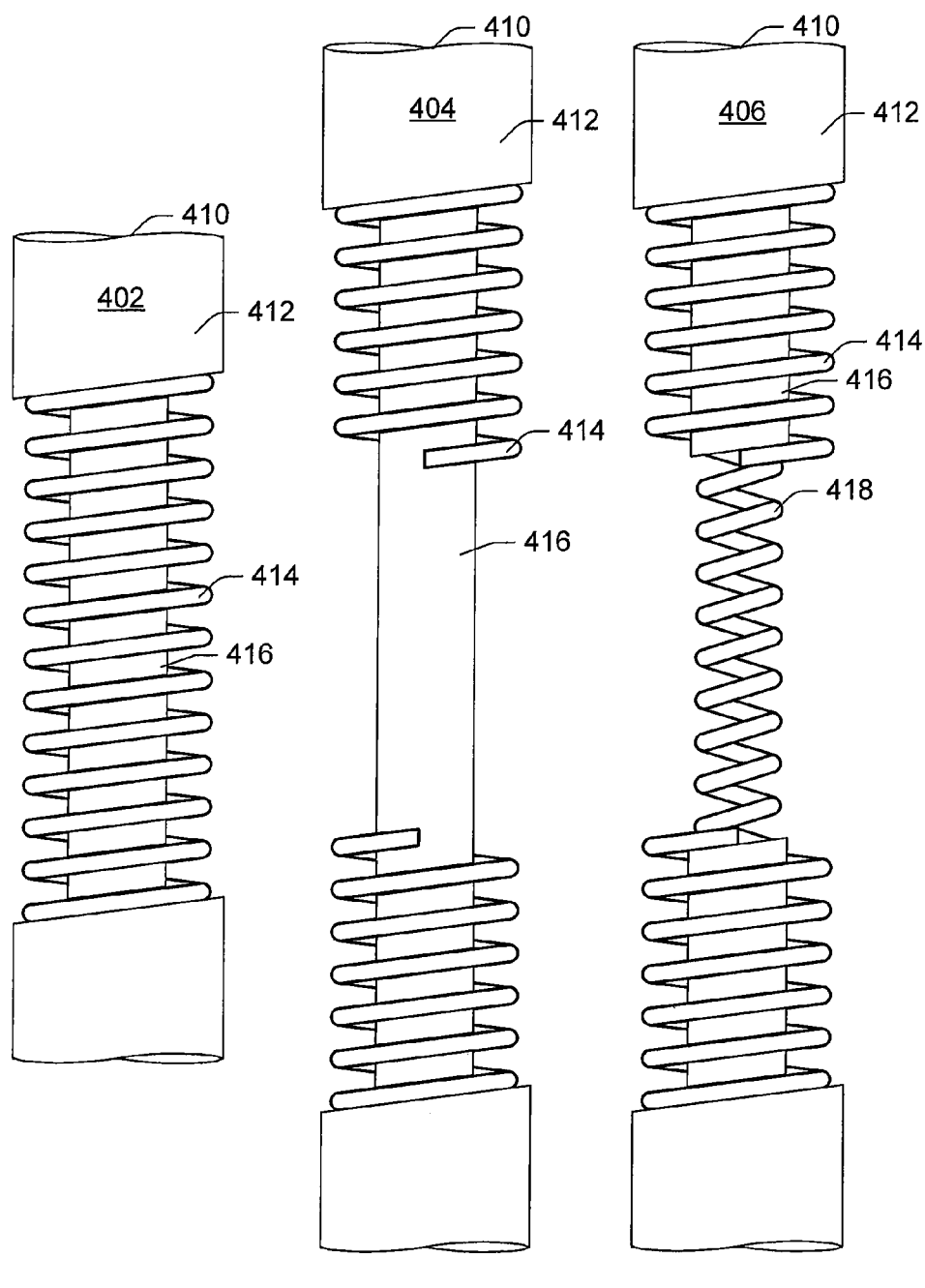
FIG. 4 is a diagram of various bipolar lead failures for a section of a lead with two conductors in a co-axial arrangement.

FIG. 4 shows several examples of lead failure for a lead 410 with a co-axial conductor arrangement. The lead 410 includes a device end for connection to an implantable device and an electrode end that continues to one or more points where electrodes may be positioned. Such a lead generally has a tip electrode and a ring electrode; however, other types of electrodes may be included. In the example 402, the lead 410 has outer insulation 412, which is absent over a length of the lead 410. The absence of the insulation 412 exposes a portion of the outer conductor 414. Additional insulation 416 isolates an inner conductor from the outer conductor 414.

In the example 404, the outer conductor 414 is broken and the insulation 416 is exposed along a portion where the outer conductor 414 has eroded or broken away. In the example 406, the insulation 416 isolating the inner conductor 418 from the outer conductor 414 has failed. In addition, the outer conductor 414 is broken and has two broken ends, one connecting to the device end and another connecting to an electrode end of the lead 410. Where the insulation 416 has failed, contact between the inner conductor 418 and the outer conductor 414 is possible. Further, where the outer conductor 414 is broken, contact with the inner conductor 418 may occur at the device-side broken end, at the electrode-side broken end or at both broken ends. Each of these circumstances can present different issues. For example, contact between the device-side broken end of the outer conductor 414 and the inner conductor 418 may result in arcing between the conductors when stimulation energy is provided. While some type of unipolar output may still be possible, the situation would normally require serious attention.

Figure 5:
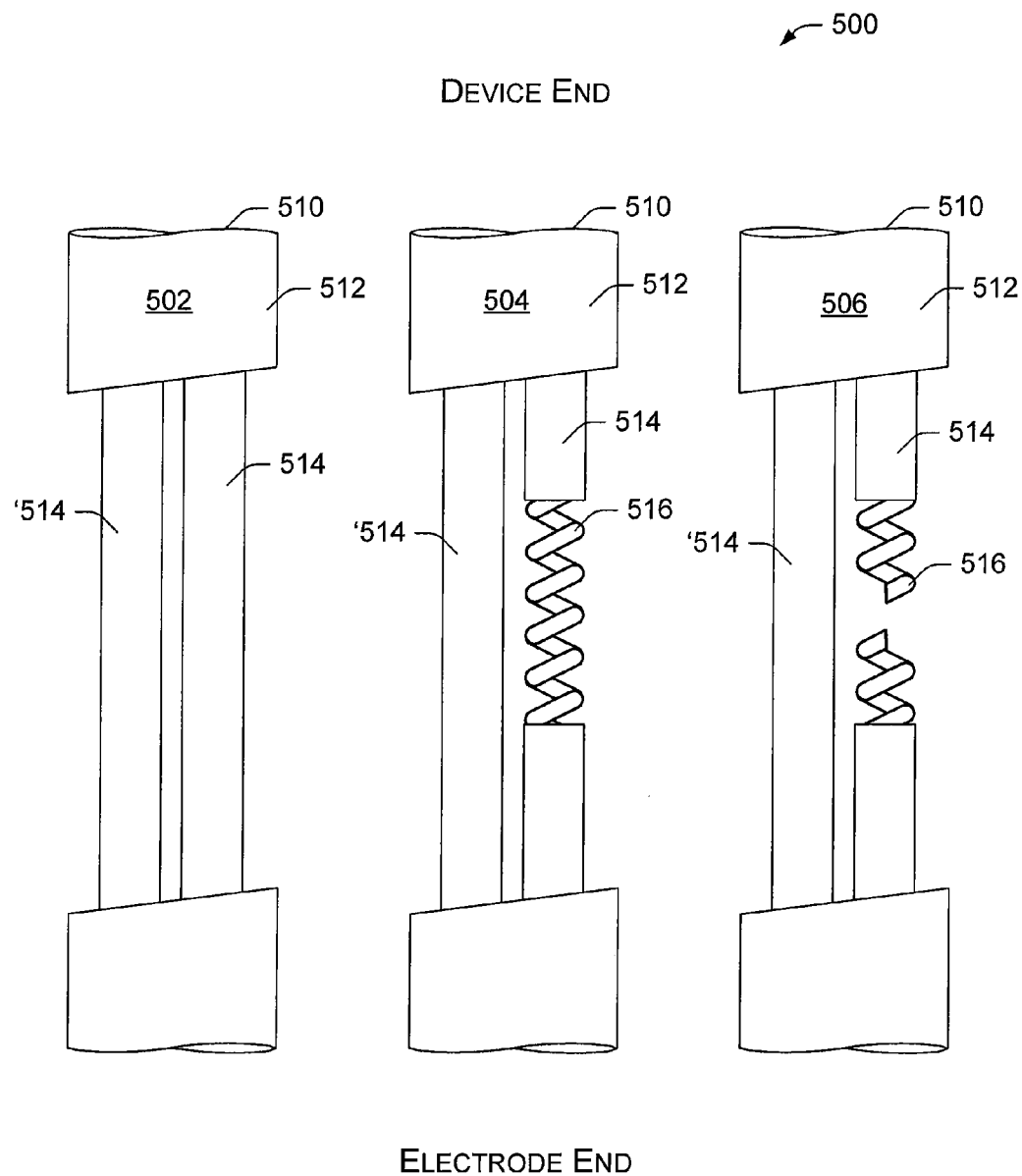
FIG. 5 is a diagram of various bipolar lead failures for a section of a lead with two conductors in a side-by-side arrangement.

FIG. 5 shows several examples of lead failure for a lead 510 with a side-by-side twin conductor arrangement. The lead 510 includes a device end for connection to an implantable device and an electrode end that continues to one or more points where electrodes may be positioned. Such a lead generally has a tip electrode and a ring electrode; however, other types of electrodes may be included. In the example 502, the lead 510 has outer insulation 512, which is absent over a length of the lead 510. Such insulation may be integral to insulation for individual conductors or separate from individual conductors. In the example 502, the absence of insulation 512 does not necessarily affect operation of insulation 514, 514' of the two conductors.

In the example 504, insulation 514 has failed thereby exposing a portion of the conductor 516. In the example 506, the conductor 516 has broken resulting in a device-side broken end and an electrode-side broken end. As described above, an exposed device-side broken end may act as an "electrode" in conjunction with a lead electrode and/or a case electrode. While not shown, similar insulation failure, lead fracture, etc., may occur for the other conductor of the lead 510. Upon failure of insulation and conductors, a complete lead separation may occur. A similar scenario may occur for the co-axial lead 410 of FIG. 4.

Common types of lead failure include insulation failure and conductor failure. Insulation failures include internal and external insulation failures. An internal insulation failure may allow for a current path or contact between two or more internal conductors of a lead. An external insulation failure may allow for a current path between an electrode and an exposed portion of a conductor. Of course, an external insulation failure may expose more than one conductor of a lead when there are side-by-side conductors.

With respect to an internal insulation failure, very low impedance may result. For example, oversensing and low lead impedance on a ventricular lead may stem from a break in insulation between a proximal conductor (proximal with respect to the closer of the two pacing electrodes to the pulse generator, usually the outer conductor in a coaxial lead) and a distal electrode (distal with respect to the conductor going to the electrode that is furthest from the implanted device—this is usually the tip electrode and in the lead itself, the inner conductor coil in a coaxial design) wherein the electrodes are used in a bipolar electrode configuration for ventricular stimulation. In some instances, the terms "distal" and "proximal" may refer to conductor cross-sectional position (e.g., outer co-axial is proximal and inner co-axial is distal); however, as explained in FIGS. 4 and 5, inner and outer may be used for co-axial conductor arrangements, left and right for side-by-side conductor arrangements, and/or other positional descriptions for any of a variety of arrangements for a lead that includes more than one conductor. Some leads may include more than two conductors.

While an x-ray may demonstrate a deformity in a conductor, insulation is typically radiolucent, and an insulation abnormality would not be readily detected using x-ray techniques. In some instances, a device may prevent x-ray visualization of a portion of lead.

With respect to a conductor failure, an excessively high lead impedance representative of an open circuit may be measured or otherwise detected. If another conductor remains intact, then unipolar stimulation and/or detection may be possible. For example, if a proximal conductor used in a bipolar electrode configuration has failed, a distal conductor may be available for use in a unipolar electrode configuration. In such an example, non-invasive intervention is typically required to reprogram a device to use the distal conductor in a unipolar electrode configuration. Normally, a unipolar output electrode configuration has lower impedance than a bipolar output electrode configuration; thus, a bipolar configuration that has lower impedance than a unipolar configuration or unusually low impedance may indicate a problem or a developing problem. For example, if unipolar impedance is higher than bipolar impedance, an insulation breach may have developed between the proximal and distal conductor. If bipolar impedance becomes markedly elevated and unipolar impedance is normal, then a conductor fracture of a proximal conductor may be developing. In bipolar co-axial leads, the proximal (outer) conductor is usually affected before the distal (inner) conductor.

Various exemplary methods optionally include impedance tracking that may track changes and call for action when impedance becomes too high, too low, etc. Again, high impedance is generally associated with an open circuit while low impedance is generally associated with a short circuit. Of course, depending on electrode configuration and conditions, a variety of impedance trends, behaviors, measurements, etc., may exist. FIG. 6 includes a table that illustrates a variety of conditions for a two conductor lead.

In C1, insulation for both lead conductors is intact and the lead conductors are intact, which represents the normal condition. In C2, the insulation for conductor 1 has failed while the other conditions are normal. In this instance, impedance may decrease between two electrodes as another path current becomes available. In C3, both the insulation for conductor 1 and conductor 1 have failed. In this instance, any distal electrodes connected to conductor 1 are rendered useless, instead, an exposed end of the conductor, if available, may result in another current path. For example, a bipolar stimulation pulse that intends to have a current path between two distal electrodes may instead have a current path between an exposed broken end of a conductor and a distal electrode associated with another conductor. If the conductor break is near the case of an implanted device, then the stimulation vector may be similar to that of a unipolar stimulation pulse.

In C4, conductor 1 and its insulation have failed along with the insulation of conductor 2. In this instance, a stimulation pulse may short between a broken end of conductor 1 and an exposed surface of conductor 2, alternatively, a stimulation pulse may short between an exposed surface of conductor 2 and a case electrode. Such a pulse is unlikely to stimulate tissue near a distal electrode within the heart connected to conductor 2 and is likely to stimulate tissue near the exposed surface, the broken end or the case electrode. In various examples, the relevant broken end of a conductor is that which is in electrical contact with an implanted device and not an end that is in electrical contact with one or more distal electrodes.

In general, any unintended alternative pathway that can divert current from its intended pathway or destination may be considered a problem. An unintended alternative pathway may have a lesser, an equal or a greater resistance than an intended pathway. A short is generally a pathway of comparatively low resistance (e.g., conductors in contact, a small gap, etc.).

In C5, insulation for conductor 1 and for conductor 2 has failed along with conductor 1 and conductor 2. In this instance, a stimulation pulse will either short between broken ends, possibly resulting in arcing between the ends (e.g., at energy levels typical of defibrillation), or include a current path with a case electrode. In this instance, stimulation therapy should not be attempted.

In C6, conductor 1 has failed without a corresponding insulation failure for conductor 1. Where such an issue is encountered, there is no exposed broken end of conductor 1 and resistance should be quite high, for example, representative of an open circuit.

In C7, conductor 1 has failed without a corresponding insulation failure; however, insulation for conductor 2 has failed. For example, in a co-axial arrangement, an outer conductor may fail and compromise the insulation for an inner conductor. While this may be viewed as a failure of insulation for the outer conductor, generally a failure is with respect to an outer environment. In another example, consider a co-radial or side-by-side arrangement wherein insulation for one conductor has failed and another conductor has failed without an insulation failure. In this example, an exposed surface of the intact conductor may decrease impedance for a selected electrode configuration.

In C8, insulation for conductor 1 has failed, conductor 1 has failed and conductor 2 has failed without a failure in its insulation. In comparison with C5, a short between the broken ends of the two conductors is unlikely because the insulation for conductor 2 is still intact.

In C9, insulation for conductor 2 has failed and exposed conductor 2 to a physiologic environment. In this instance, a new current path may be available between the exposed surface of conductor 2 and a case electrode or other electrode in electrical contact with conductor 1. In C10, insulation for conductor 1 and for conductor 2 has failed. In this instance, a short may occur between the two conductors, especially if the insulation failure is at approximately the same location on a lead. As already mentioned, arcing may occur and thereby permanently short the two conductors.

In C11, insulation for conductor 1 has failed along with insulation for conductor 2 and conductor 2. In this instance, physical contact between a broken end of conductor 2, having an electrical connection to an implanted device, and an exposed surface of conductor 1 may cause a short, arcing, etc. In C12, insulation for conductor 1 has failed along with conductor 2. If a stimulation pulse is delivered using conductor 1, a current path may exist between an exposed surface of conductor 1 and the case of an implanted device. In general, conductor 2 will be open and unable to deliver a stimulation pulse.

In C13, conductor 1 has failed and conductor 2 has failed while insulation remains intact for both conductors. While this condition may seem rare, such failures may result from differences in material properties of the insulation and the conductors. For example, if a metal is exposed to a cold temperature and shock, it may break more readily than a polymeric material. Of course, fatigue characteristics may differ between insulation and conductor materials whereby certain stress and frequency exposures cause failure of a conductor prior to failure of insulation.

In C15, insulation for conductor 2 has failed along with conductor 2. In this instance, a broken end and/or exposed surface of conductor 2 may provide a current path that compromises delivery of a therapeutic stimulus. In C16, conductor 1 has failed along with insulation for conductor 2 and conductor 2. In this instance, insulation for conductor 1 remains intact while a broken end and/or exposed surface of conductor 2 may provide a current path that compromises delivery of a therapeutic stimulus.

In various instances where external insulation has failed, fluid may enter the lead. If a conductor fracture has occurred, then such fluid may act as a conductor, generally with an increase in impedance for the conductor. If internal insulation has failed, then such fluid may act to short two conductors.

Various conditions may cause affect battery current drain, for example, if no pulse can be delivered and an implanted device discontinues delivery, battery longevity may be extended. In contrast, if a high output is set due to a lead problem, then battery current drain may increase drastically and thereby shorten battery life. In either instance, battery condition may be monitored to provide at least some indication of lead condition. Intermittent lead failures may at times be evidenced by battery condition or history of battery condition.

Lead condition can affect capture and/or one or more settings that aim to achieve capture. Capture may be defined as a cardiac depolarization induced by a stimulus or output pulse; the resulting capture may also be termed an "evoked response". Another term, "capture threshold" is typically defined as the lowest output setting that results in stable and consistent capture. While capture may be reported in terms of energy, charge and current density, these cannot be directly or easily measured nor directly programmed in a clinical setting. Often, capture threshold is defined by programmable options of a pacing device or system. Many pacing systems report capture threshold in terms of pulse amplitude (e.g., volts) or pulse duration (e.g., milliseconds). Another term for pulse duration is pulse width. Where voltage is mentioned with respect to output stimulation settings for particular algorithms, energy may be inferred and hence other suitable manners to increase energy output may be substituted.

With respect to effect of lead condition on capture, for example, a marked rise in capture threshold and/or loss of capture with or without under- or oversensing may be due to a change in lead condition. Oversensing is typically defined as the detection of nonphysiologic or inappropriate physiologic signals. While oversensing is more common with unipolar (e.g., larger sensing "antenna"), it may occur in bipolar sensing configurations as a result of extraneous electro-magnetic interference (e.g., electronic article surveillance, electrocautery, etc.). Of course, physiologic or "systemic" conditions may affect capture as well. Systemic conditions include conditions associated with interface between an electrode and tissue, fluid, etc., and conditions related to patient metabolism, fluid balance, drugs, etc.

Table 2A and Table 2B, below, include information as to possible consequences of mechanical problems with a lead as to capture, evoked response detection, impedance and stimulus artifact amplitude.

TABLE 2A

Exemplary Possible Consequences, Bipolar

| Malfunction | Capture Threshold | ER Detection | Impedance | Artifact Amplitude |
|---|---|---|---|---|
| Bi (Normal) | Normal | Normal | Normal | Small |
| Partial Prox. Fracture | Increase | Normal | Increase | Decreased |
| Total Prox. Fracture | Infinitely high | Loss | Infinitely high | Absent |
| Ext. Insul. Breach | Normal | Decrease | Mild decrease | Increased |
| Int. Insul. Breach | Increase | Decrease | Sig. decrease | Decreased |

TABLE 2B

Exemplary Possible Consequences, Unipolar

| Malfunction | Capture Threshold | ER Detection | Impedance | Artifact Amplitude |
|---|---|---|---|---|
| Uni (Normal) | Normal | Normal | Normal | Large |
| Ext. Insul. Breach | Increase | Decrease | Normal/Mild decrease | Decrease |
| Partial Cond. | Increase | Normal | Increase | Decrease |
| Total Fracture of Cond. | Infinitely high | Loss | Mild increase | Decrease but present |
| Total and Insul. OK | Increase | Normal/Mild decrease | Increase | Sig. decrease |

Observation of any of such conditions may aid in determining a proper course of action with respect to therapy.

Figure 7:
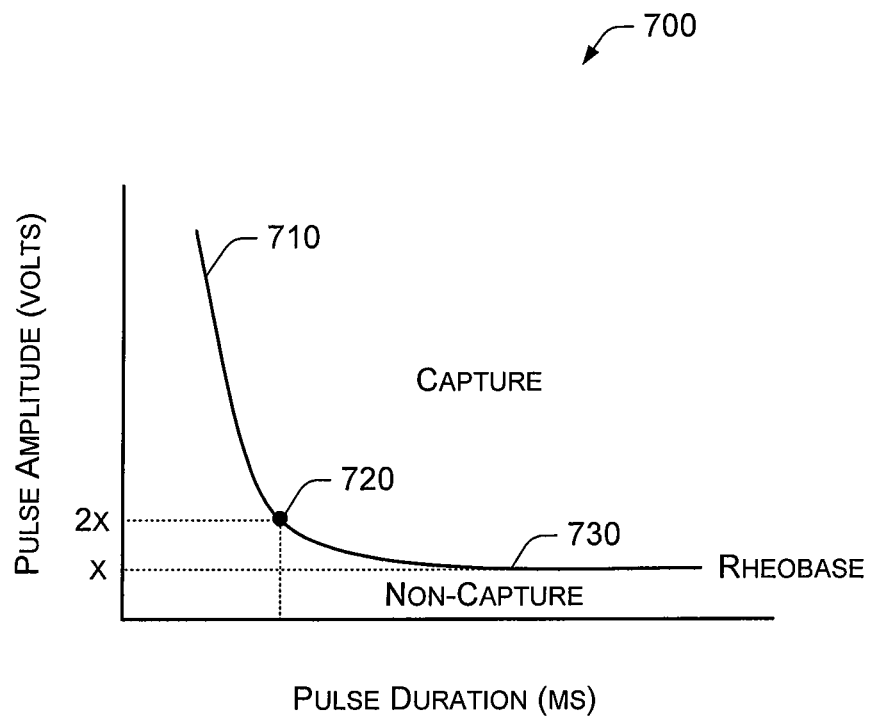
FIG. 7 is an exemplary plot of pulse amplitude versus pulse duration or pulse width.

FIG. 7 shows a plot 700 of pulse amplitude versus pulse duration and a "strength-duration" curve 710. If output falls to the left of and/or below the curve 710, it will be subthreshold and there will be loss of capture. If output coincides with or falls to the right and/or above of the curve 710, capture should be present. The strength-duration curve 710 indicates that pulse amplitude must be high for extremely narrow pulse width or short duration to cause capture. At some point, typically around 1 ms, the pulse amplitude plateaus and does not decrease further despite additional increases in pulse duration. The plateau is typically referred to as the rheobase and the threshold at twice the rheobase is typically referred to as the chronaxie point.

Some pacing systems use algorithms that aim to automatically adjust output and/or assess capture threshold, usually on a periodic basis. A particular system uses the AUTOCAPTURE™ algorithm (St. Jude Medical, Cardiac Rhythm Management Division, Sylmar, Calif.) to automatically monitor capture on a beat-by-beat basis, provide a high output back-up pulse in the setting of loss of capture associated with the primary output pulse and adjust output and/or assess capture threshold on both a scheduled and on an as-needed basis. In general, such algorithms place patient safety ahead of battery current drain; however, when the chronic threshold is low, this algorithm also minimizes battery current drain, effectively increasing device longevity.

The AUTOCAPTURE™ algorithm runs a capture threshold assessment test once every eight hours. To perform this test, the paced and sensed AV delays are temporarily shortened to about 50 ms and to about 25 ms, respectively. The AUTOCAPTURE™ algorithm generally uses a bottom-up approach (also referred to as an "up threshold") and a back-up pulse for safety when an output pulse does not result in capture. With respect to use of a back-up pulse, an output pulse of about 4.5 volts is typically sufficient to achieve capture where lead integrity is not an issue. Use of a back-up pulse may also adequately benefit certain patients that are quite sensitive to loss of capture. For example, patients having a high grade AV block may be sensitive to protracted asystole. Even if loss of capture is recognized immediately and adjustment is completed in less than about 1 second, a patient may still have been asystolic for over 2 seconds utilizing a standard capture threshold test. A back-up pulse typically prevents occurrence of such a long asystolic period. However, conventional autocapture threshold/detection algorithms do not attempt to detect the evoked response directly related to capture of the back-up. Thus, the assumption that a back-up pulse resulted in capture is generally not tested. Various exemplary methods described herein optionally include evoked response detection of the back-up pulse to help determine if a back-up pulse caused an evoked response thus confirming the presence of capture associated with this stimulus. Such ER detection may be implemented for a unipolar back-up pulse and/or a bipolar back-up pulse.

In general, the term "sensing" is often utilized with respect to the pacemaker recognizing native atrial and/or ventricular depolarizations. While technically, detection of an evoked response ER relies on or includes "sensing", an implantable device often uses a separate circuit for ER detection. Throughout, the term "ER detection" may be used in place of sensing when specifically concerned with, for example, an autocapture algorithm and recognition of capture.

With respect to ER detection, various exemplary methods use a unipolar primary pulse with bipolar ER detection, a unipolar primary pulse with unipolar ER detection, a bipolar primary pulse with bipolar ER detection, a bipolar primary pulse with unipolar ER detection and/or no primary pulse ER detection. Various exemplary methods use a unipolar back-up pulse with bipolar ER detection, a unipolar back-up pulse with unipolar ER detection, a bipolar back-up pulse with bipolar ER detection, a bipolar back-up pulse with unipolar ER detection and/or back-up pulse ER detection.

Regarding AUTOCAPTURE™ algorithms, the first generation algorithm was implemented using a unipolar output configuration and a bipolar detection configuration. Where insulation and/or fracture issues arise for a proximal conductor (bipolar detection), an evoked response may not be sensed and, in turn, result in delivery of a high voltage back-up pulse and a ramping up of the primary output voltage (e.g., energy via voltage, pulse width, etc.). A capture threshold history may exhibit some information that relates to such a problem. In particular, a history may help to identify intermittent problems (e.g., sporadic increases in reported capture threshold where the actual unipolar capture threshold is relatively stable).

In clinical follow-up, a care provider may perform a threshold test to determine if the algorithm for capture is working properly and for further assessment. In systems that use the AUTOCAPUTRE™ algorithm, a follow-up clinical test includes automatically and temporarily setting PV delay and AV delay intervals to about 25 ms and about 50 ms, respectively. Shortening of the AV and PV delays acts to minimize risk of fusion. Fusion may compromise measurement and detection of an ER signal, especially ER signal amplitude. If results from the follow-up test indicate that enabling of the algorithm would not be safe due to too low an evoked response or too high a polarization signal, then the algorithm may be disabled and a particular, constant output programmed to achieve capture with a suitable safety margin. If the ER and polarization signals are appropriate to allow an autocapture algorithm to be enabled, an ER sensitivity will be recommended by the programmer and may then be programmed as it relates to detection of an ER signal.

The follow-up tests typically work top down. If loss of capture occurs, a first output adjustment step typically sets a high output and then decreases output by about 0.25 volts until loss of capture occurs (also referred to as a "down threshold"). At this point, output is increased in steps of a lesser amount (e.g., about 0.125 volts) until capture occurs. Once capture occurs, a working or functional margin of about 0.25 volts is added to the capture threshold output value. Hence, the final output value used is the capture threshold plus a working margin. Systems that use a fixed output use a safety margin ratio instead of an absolute added amount. The safety margin is a multiple of the measured capture threshold, commonly 2:1 or 100% to allow for fluctuations in the capture threshold between detailed evaluations at the time of office visits.

With respect to a down threshold approach, in instances where loss of capture occurs, a first output adjustment step typically increases output until capture is restored. Steps used in the AUTOCAPTURE™ algorithm are typically finer than those used in a routine follow-up capture threshold test. At times, a down threshold algorithm may result in a threshold that is as much as 1 volt lower from the result of an up threshold algorithm. This has been termed a Wedensky effect. In general, an actual output setting (e.g., including safety margin) may be adjusted to account for whether a patient is pacemaker dependent. In a patient who is not dependent on the pacing system, a narrower safety margin may be selected than would be the case for a patient whom the physician considers to be pacemaker dependent.

As already mentioned, lead instability may affect capture threshold, similarly, capture threshold history may help to identify lead instability. Lead instability includes issues germane to failure as well as issues germane to movement of a lead (e.g., to cause movement of an electrode of the lead, etc.). A stable capture threshold history may indicate normal lead function. However, marked fluctuations in capture threshold over time may indicate a lead stability problem, such as movement and variations with the degree of contact between the electrode and endocardial tissue. If the problem is associated with movement, repositioning or re-anchoring may be required. If such fluctuations occur in the early post-implant period, the problem may relate to positional instability as opposed to a marked inflammatory reaction at the electrode-tissue interface (e.g., "lead maturation"). As described herein, various exemplary methods may distinguish positional instability issues from lead failure issues (e.g., mechanical degradation, etc.). Such exemplary methods may include use of capture threshold information.

Figure 8:
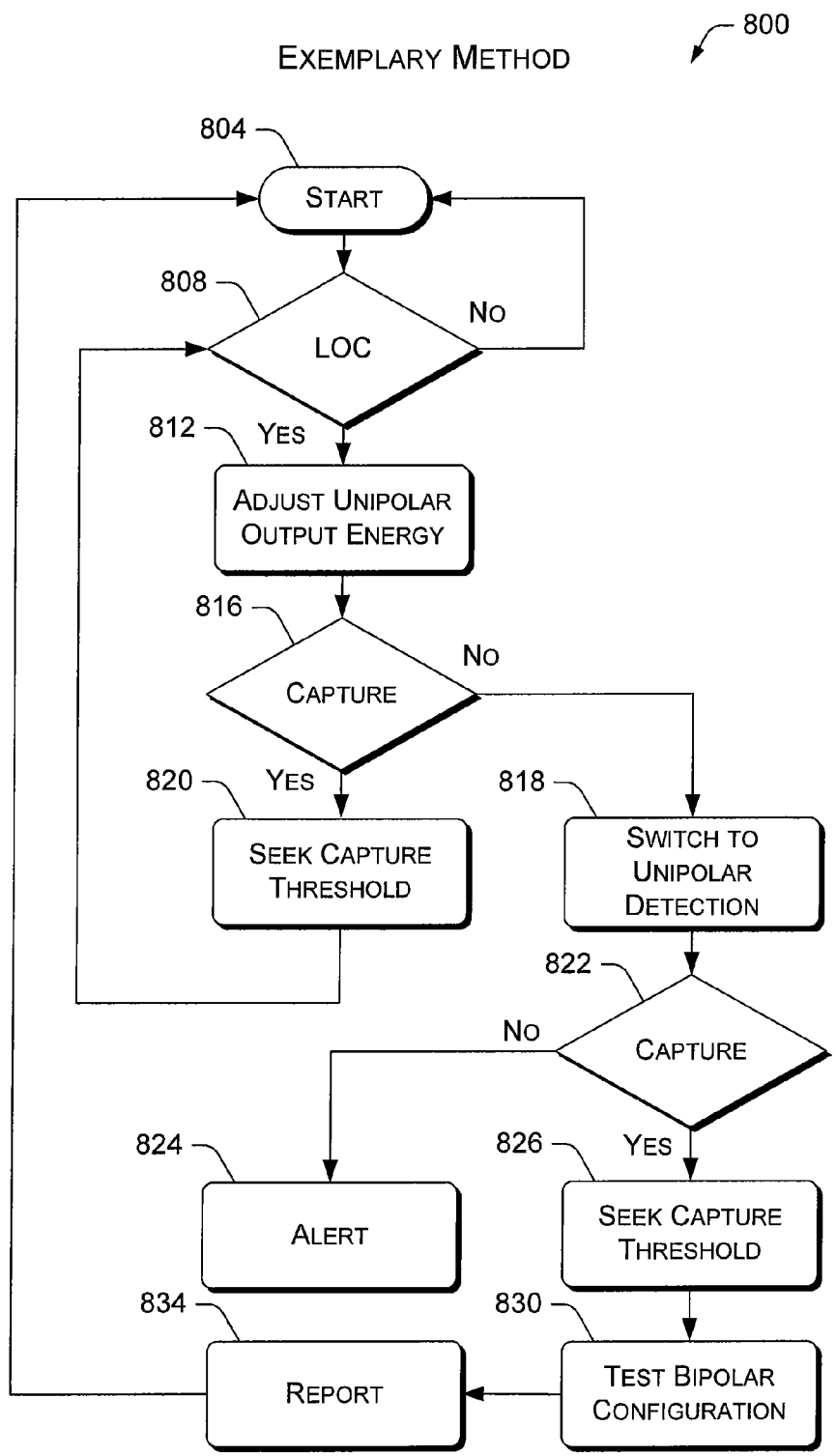
FIG. 8 is a block diagram of an exemplary method for using capture information to aid in diagnosis of lead condition.

FIG. 8 shows an exemplary method 800 that can provide information regarding lead condition. The method 800 commences in a start block 804 wherein a unipolar electrode configuration is used to deliver an output pulse. A decision block 808 follows that decides if loss of capture has occurred based on information sensed using a bipolar electrode configuration. For example, a bipolar electrode configuration may be capable of detecting an evoked response, responsive to the output pulse delivered using the unipolar electrode configuration. If no evoked response or an insufficient signal is sensed, then loss of capture may be indicated, alternatively, more than one such occurrence may be noted prior to indicating that a loss of capture has occurred. For example, regarding the latter, two consecutive cycles of output and insufficient signal may be required prior to indicating that loss of capture has occurred.

The exemplary method 800, as well as various other exemplary methods, may determine whether capture occurred by implementing evoked response detection for a particular output pulse or cardiac stimulus. As mentioned, evoked response detection relies on or includes "sensing" and therefore depends on an electrode configuration (e.g., unipolar, bipolar, etc.). Evoked response detection can determine whether an evoked response occurred, i.e., whether capture occurred. Various exemplary methods implement evoked response detection for a particular cardiac stimulus whether the stimulus is monophasic, biphasic, multiphasic, a train of multiple stimuli aimed at causing a single cardiac event, etc. As described herein, a pulse is a stimulus, which may be monophasic, biphasic, multiphasic, a train of multiple pulses aimed at causing a single cardiac event, etc.

Referring again to FIG. 8, if capture has not been lost, then the exemplary method 800 may continue at the start block 804. However, if the decision block 808 indicates that a loss of capture has occurred, then the method 800 continues in an output adjustment block 812. The output adjustment block 812 adjust the unipolar output energy upward, for example, to a value that is likely to result in capture, assuming no lead issues and appropriate delivery timing (e.g., the pulse is not delivered during a physiologic refractory period). The aim of the unipolar delivery at a higher energy level may be two-fold: to test integrity of the lead and to ensure capture if lead integrity is not an issue. In other words, if the unipolar configuration is incapable of delivering stimulation that causes an evoked response, then a lead problem is highly likely for the unipolar configuration.

Another decision block 816 follows wherein ER detection information is analyzed to decide if the unipolar output per the adjustment block 814 caused an evoked response. According to the exemplary method 800, the sensed information is acquired using a bipolar electrode configuration. In other examples, a unipolar electrode configuration may be used. Alternatively, or in addition to such configurations, another sensor (e.g., physiologic sensor 270) may be used to determine if the higher energy unipolar stimulation caused an evoked response. For example, a hemodynamic sensor may show an appropriate increase or decrease in blood pressure following delivery of the higher energy unipolar stimulation. Use of two indicators may aid in diagnosis of lead issues. For example, if a hemodynamic sensor indicates capture and a bipolar ER detection system fails to indicate capture, then either a false positive occurred for the hemodynamic sensor or a false negative occurred for the bipolar ER detection system, possibly due to a lead issue.

If the decision block 816 indicates capture, then the method 800 may continue in a threshold adjustment block 820 or another appropriate block. However, if the decision block 816 indicates a lack of capture, then the method 800 continues in a switch block 818 that switches the electrode configuration for ER detection from bipolar to unipolar. Thus, the block 818 ensures that output and ER detection use a unipolar electrode configuration. The premise being that the lack of capture at the decision block 816 could be a result of inadequate bipolar ER detection, for example, a problem with a lead, a conductor, an electrode, etc., associated with the bipolar electrode configuration. Yet another decision block 822 follows that decides if the unipolar output resulted in an evoked response (e.g., capture). In general, the decision block 822 relies on sensed information such as information sensed using the unipolar electrode configuration and/or a physiologic sensor (e.g., the physiologic sensor 270).

If the decision block 822 indicates no capture, then the method 800 continues in an alert block 824 that may mark an alert, alert a patient, a care provider (e.g., via a network, etc.). However, if the decision block 822 indicates that capture occurred, then the method 800 continues in a seek capture threshold block 826 which seeks a capture threshold/appropriate output for the unipolar electrode. The method 800 optionally includes a configuration maintenance block, which may, for example, prevent a switch to a bipolar electrode configuration for output and/or detection. In another alternative, such an exemplary method may provide back-up using a unipolar electrode configuration and seek a capture threshold for a bipolar electrode configuration. If the seeking uses an up threshold approach and the output energy ramps up to a maximum without any indication of capture, then the method may confirm that an issue exists with the bipolar electrode configuration (e.g., a lead problem). A similar result may occur for a down threshold approach wherein no programmable energy output causes capture.

As shown, the exemplary method 800 enters a bipolar configuration test block 830 for testing the bipolar lead for conditions such as insulation, conductor and/or other failures. A report block 834 follows for reporting appropriate test results. Thereafter, the method 800 may continue at the start block 804 or with other action.

With respect to the capture threshold search blocks 820, 826, in either or both instances, adjustments to AV and/or PV delay may occur to avoid fusion, which can obfuscate information required for capture detection. These delays may be shortened and/or extended, as appropriate.

The exemplary method 800 can allow for a relatively expedient diagnosis of lead-related issues. In comparison to a conventional method, a capture threshold search may take about 20 seconds before reaching a maximum adjustable/programmable output and concluding that a problem exists. During this time, a back-up may or may not be operating properly and, if one is, it is likely that the output will be set at a fairly high energy level.

Some patients are sensitive to high output unipolar pulses due to, for example, pectoral muscle stimulation near the case of a device (e.g., "pocket stimulation"), which can be a motivation for initially using a bipolar electrode configuration for back-up pulses. However, local muscle contractions at or near the "pocket" may be indication for a patient that a unipolar output pulse is being used. Of course, other conditions may cause a patient to experience such sensation. For example, if a proximal conductor acting as a return for a bipolar electrode configuration and its external insulation has failed at a location near the case of an implanted device, then a patient may experience a sensation similar to pocket stimulation where a broken, exposed end of the proximal conductor acts as the return electrode as opposed to a distally located electrode connected to the faulty proximal conductor. As already mentioned, contact between a lead and a case may cause failure and a crush of the lead between the clavicle and first rib may cause failure; both of these failures may, in some instances, cause muscle stimulation or sensation near the pocket. In general, if such a problem arises, impedance measurements may show that bipolar electrode configuration impedance is abnormally close to that of unipolar electrode configuration impedance.

Table 3 below includes a variety of scenarios and abbreviations wherein back-up pulse ER detection may not occur or occur via unipolar or bipolar electrode configurations. Further, one or more other sensors may be available to help determine if a primary and/or a back-up pulse resulted in capture.

TABLE 3

Exemplary Scenarios

| | Abbreviation | Primary | ER detection | Back-up |
|---|---|---|---|---|
| S1 | U/Bi-Bi | Unipolar | Bipolar | Bipolar |
| S2 | U/Bi-U | Unipolar | Bipolar | Unipolar |
| S3 | U/U-Bi | Unipolar | Unipolar | Bipolar |
| S4 | U/U-U | Unipolar | Unipolar | Unipolar |
| S5 | Bi/U-Bi | Bipolar | Unipolar | Bipolar |
| S6 | Bi/U-U | Bipolar | Unipolar | Unipolar |
| S7 | Bi/Bi-Bi | Bipolar | Bipolar | Bipolar |
| S8 | Bi/Bi-U | Bipolar | Bipolar | Unipolar |

Seven of the eight scenarios include use of a bipolar electrode configuration. For example, assuming a co-axial arrangement where a distal conductor is used for unipolar electrode configurations, failure of a proximal conductor used as a return (insulation intact) for the U/Bi-Bi scenario will result in a failure to detect loss of capture and an ability to deliver back-up pulses.

Figure 9:
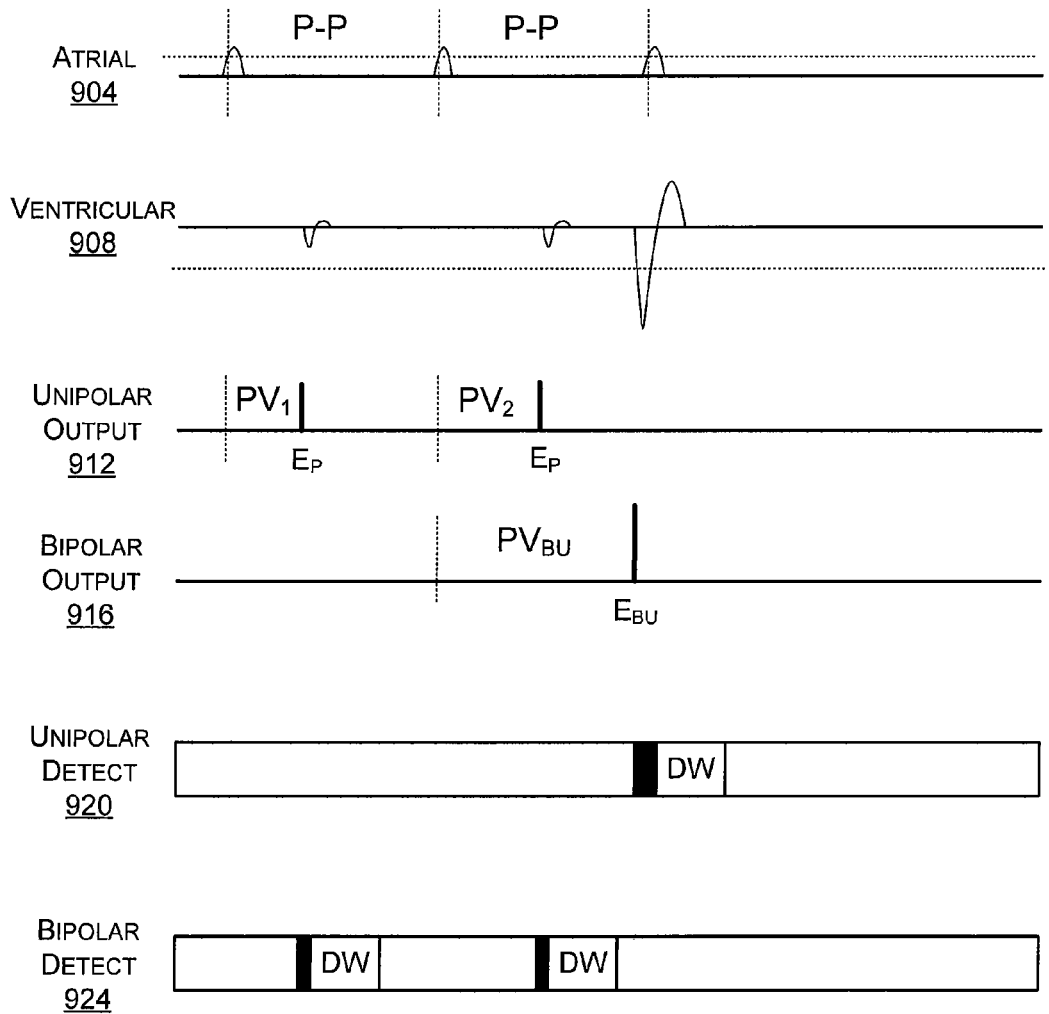
FIG. 9 is a schematic of an exemplary scenario that includes use of unipolar primary output, bipolar evoked response detection and bipolar back-up output.
Figure 10:
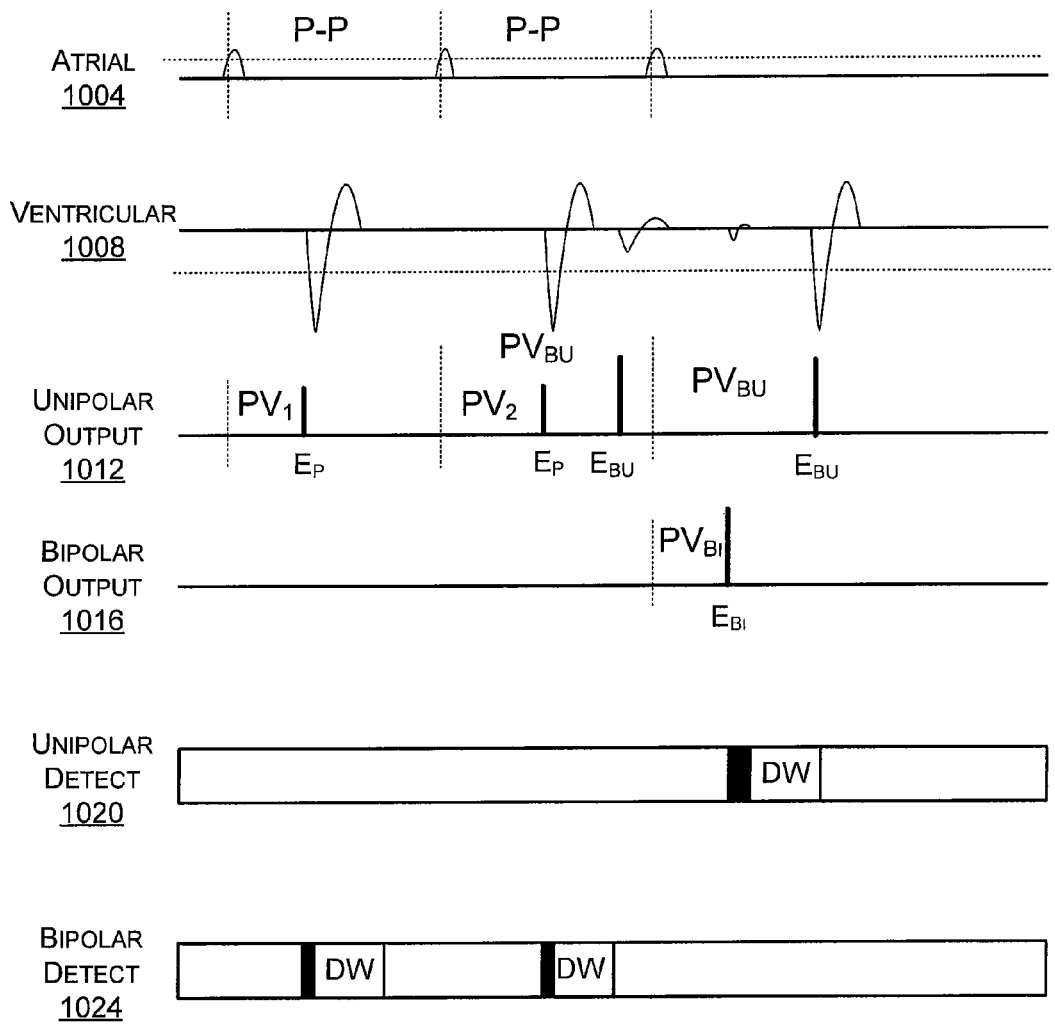
FIG. 10 is a schematic of an exemplary scenario that includes use of unipolar primary output, bipolar evoked response detection and unipolar back-up output.
Figure 11:
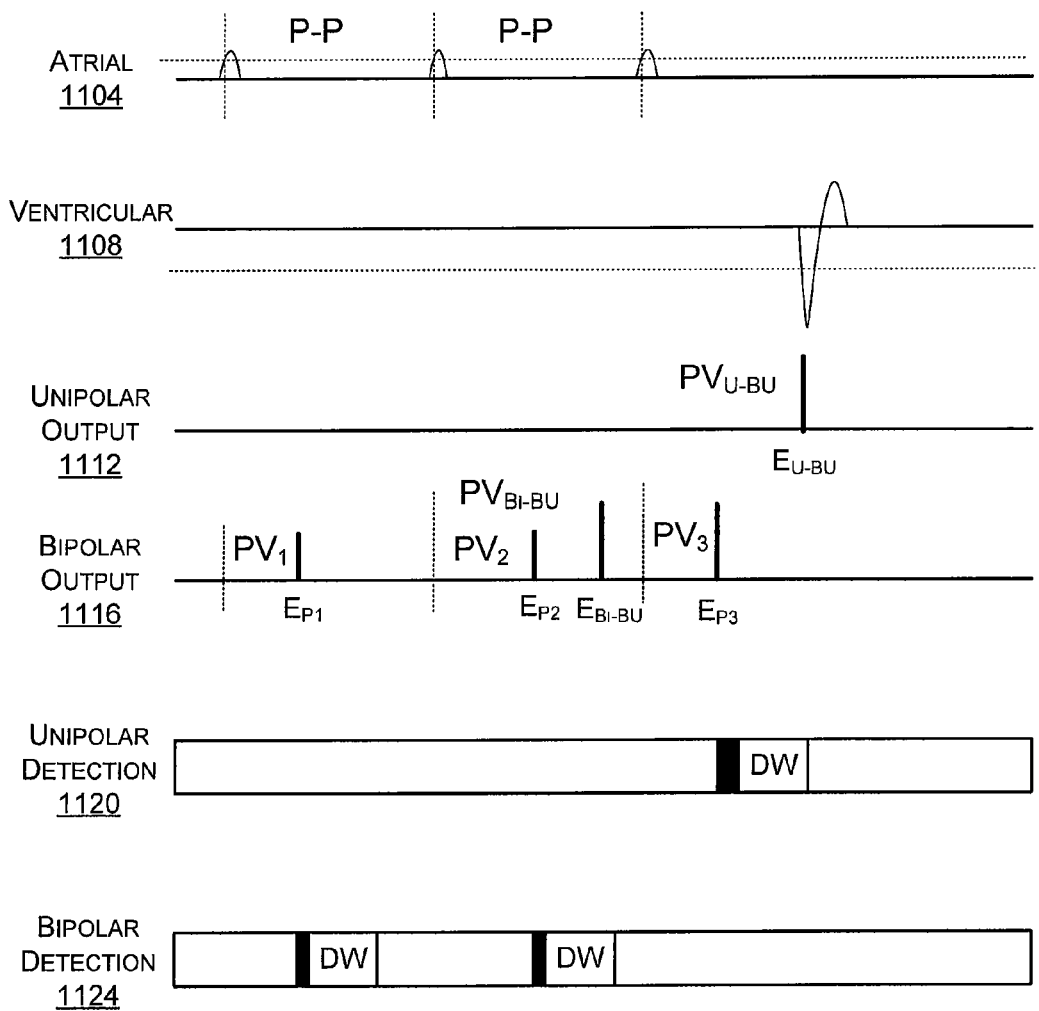
FIG. 11 is a schematic of an exemplary scenario that includes use of bipolar primary output, bipolar evoked response detection and bipolar back-up output.

FIGS. 9, 10 and 11 show various exemplary scenarios that use a bipolar electrode configuration to sense information related to capture. FIG. 9 shows an exemplary scenario 900 that initially uses a unipolar primary output with bipolar ER detection and a bipolar back-up pulse. The use of a bipolar back-up pulse may help minimize sensation associated with delivery of a back-up pulse. For example, a patient may tolerate normal pacing energies of a unipolar primary pulse but not comfortably tolerate higher back-up pacing energies delivered using a unipolar electrode configuration.

The exemplary scenario 900 is exhibited through use of an atrial activity line 904, a ventricular activity line 908, a unipolar output line 912, a bipolar output line 916, a unipolar ER detection line 920 and a bipolar ER detection line 924. The detection lines 920 and 924 indicate where evoked response detection may be implemented. Various lines may represent channels of an implantable device such as an input or an output channel. The atrial activity line 904 indicates that a patient has intrinsic atrial activity occurring on a fairly regular basis. However, as indicated by the ventricular activity line 908, there is insufficient AV conduction or another problem whereby ventricular pacing is required. The ventricular activity line 908 also includes a dashed line that represents a level represented of an evoked response. For example, if a waveform on the ventricular activity line 908 does not have sufficient amplitude to cross the level, then even if sensing is intact, the response will not be considered as an evoked response. The unipolar output line 912 shows delivery of a first primary ventricular stimulus at an energy $E_P$ using a PV interval $PV_1$. The bipolar ER detection line 924 shows a corresponding blanking period and detection window, DW. As shown on the ventricular activity line 908, the unipolar output at energy $E_P$ may have caused some depolarization; however, the activity has an insufficient magnitude. Thus, as the signal is sensed during the detection window of the bipolar ER detection line 924, a determination of no capture would result.

In this scenario, an implanted device may consider that the output energy was too low and hence, it was subthreshold. This may occur in association with fusion, or that a problem exists with bipolar ER detection. Again, as already discussed, a "loss of capture" may be recognized after one or more failures to detect a suitable evoked response. For example, failure to detect a single evoked response may be due to fusion whereby an adjustment is then made to an AV or PV delay time; whereas, failure to recognize two consecutive evoked responses, especially where an adjustment has been made to avoid fusion, is typically a better indicator that capture has been lost, assuming that there are no detection issues (i.e., lead issues, electrode issues, sensitivity issues, etc.).

Referring again to the scenario 900, upon failure to sense an evoked response, another unipolar output at energy $E_P$ is delivered using an extended PV delay, $PV_2$. As with the first instance, bipolar ER detection is used to determine if the unipolar primary output captured; however, again, a failure to capture is indicated and a bipolar back-up pulse delivered at energy $E_{BU}$ and with a PV delay of $PV_{BU}$, which may be based on a timeout of the bipolar detection window (DW) for the primary pulse. In this example, unipolar ER detection is used to determine if the back-up pulse captured.

Consequences of this particular algorithm are confirmation of proper bipolar detection and stimulation output and that the unipolar capture threshold has changed, for any of a variety of reasons. While a unipolar back-up may have been able to make a similar determination, it may have contributed to patient discomfort. Further, if bipolar ER detection was used with a unipolar back-up and capture was not indicated then, based on such information, there would be no manner to determine whether a problem existed with the bipolar configuration.

FIG. 10 shows an exemplary scenario 1000 that uses unipolar primary output with bipolar ER detection and unipolar back-up. The scenario 1000 illustrates a failure in the bipolar electrode configuration wherein a bipolar primary output is used to aid in the diagnosis along with, for example, unipolar ER detection. Other sensing may be used to assess the bipolar output, such as sensing by a physiologic sensor. The bipolar output is followed by a unipolar back-up pulse if necessary.

The exemplary scenario 1000 is exhibited through use of an atrial activity line 1004, a ventricular activity line 1008, a unipolar output line 1012, a bipolar output line 1016, a unipolar ER detection line 1020 and a bipolar ER detection line 1024. The detection lines 1020 and 1024 indicate where evoked response detection may be implemented. The atrial activity line 1004 indicates that a patient has intrinsic atrial activity occurring on a fairly regular basis. However, as indicated by the ventricular activity line 1008, there is insufficient AV conduction or other problems whereby ventricular pacing is required. The ventricular activity line 1008 also includes a dashed line that represents a level represented of an evoked response. For example, if a waveform on the ventricular activity line 1008 does not have sufficient amplitude to cross the level, then even if capture occurs, the response will not be considered as a valid evoked response. This is termed evoked response undersensing and results in the delivery of an unneeded back-up pulse.

The unipolar output line 1012 shows delivery of a first primary ventricular stimulus at an energy $E_P$ using a PV interval $PV_1$. The bipolar ER detection line 1024 shows a corresponding blanking period and detection window, DW. As shown on the ventricular activity line 1008, the unipolar output at energy $E_P$ results in depolarization (e.g., a downward deviation) having amplitude sufficient for registering as an evoked response; however, the activity did not register as an evoked response on the bipolar ER detection line 1024. Thus, the exemplary algorithm implements a unipolar back-up pulse if the next primary output fails to register as an evoked response. Further, an adjustment is made to the PV delay, as indicated by $PV_2$ on the unipolar output line 1012. The adjustment may extend or shorten the delay to avoid fusion, which may not register as an evoked response.

At the appropriate delay time, a unipolar output of energy $E_P$ is delivered and bipolar ER detection is used to determine if capture occurred. As in the prior instance, the bipolar ER detection failed to sense an evoked response, consequently, a unipolar back-up pulse is delivered, for example, timed with respect to the bipolar ER detection window. As shown on the ventricular activity line 1008, the back-up pulse is delivered close in time to the primary pulse and does not result in any significant depolarization (e.g., delivered partially during a physiologic refractory period). ER detection may or may not occur for the unipolar back-up pulse. In this instance, even if ER detection was used, it may not register as an evoked response due to the close proximity to the evoked response of the primary pulse. Further, such a back-up pulse could be detrimental if it were delivered during a vulnerable period of the ventricle. Thus, with problematic bipolar ER detection, the scenario 1000 can be detrimental to maintenance of cardiac output and a stable cardiac rhythm.

In response to the failure to register an evoked response for two primary output pulses, the exemplary scenario 1000 delivers a bipolar primary pulse using an energy, $E_{Bi}$, which is normally sufficient to cause an evoked response when delivered at an appropriate time (e.g., PV delay of $PV_{Bi}$). The unipolar ER detection line 1020, indicates that unipolar ER detection is used to determine if the bipolar primary pulse caused an evoked response. Alternatively, or in addition to, other sensing (e.g., hemodynamic, etc.) may be used. In the scenario 1000, the bipolar primary pulse fails to cause an evoked response and a unipolar back-up pulse is delivered at an appropriate time, for example, based at least in part on a timeout of a detection window (DW).

In the scenario 1000, a relatively high energy bipolar primary pulse was delivered with unipolar ER detection and a unipolar back-up pulse to determine if any problems existed for the bipolar electrode configuration and to ensure that the patient did not experience any significant asystole. After determining that an issue exists for the bipolar electrode configuration, an exemplary method may disallow all uses of the bipolar electrode configuration and optionally use unipolar ER detection for adjusting output according to capture threshold (e.g., for performing a capture threshold search, etc.).

FIG. 11 shows an exemplary scenario 1100 that is exhibited through use of an atrial activity line 1104, a ventricular activity line 1108, a unipolar output line 1112, a bipolar output line 1116, a unipolar ER detection line 1120 and a bipolar ER detection line 1124. The detection lines 1120 and 1124 indicate where evoked response detection may be implemented. The atrial activity line 1104 indicates that a patient has intrinsic atrial activity occurring on a fairly regular basis. However, as indicated by the ventricular activity line 1108, there is insufficient AV conduction or other problems whereby ventricular pacing is required. The ventricular activity line 1108 also includes a dashed line that represents a level represented of an evoked response. For example, if a waveform on the ventricular activity line 1108 does not have sufficient amplitude to cross the level, then even if capture occurs, the response will not be considered as a valid evoked response.

In the scenario 1100, primary pacing occurs via bipolar lead using a bipolar electrode configuration. A first primary output occurs using a PV delay $PV_1$ and energy $E_{P1}$. To determine if the first primary output resulted in an evoked response, the scenario 1100 uses the bipolar electrode configuration to detect an ER signal, per the bipolar detection line 1124. The ventricular line 1108 indicates that the called for output resulted in no ventricular activity. Again, as already mentioned, failure to detect an evoked response may be due to one or more factors such as fusion, insufficient output energy, insufficient sensing parameters, lead instability, compromised lead integrity, etc.

In response to the failure to detect an evoked response, the scenario 1100 calls for another bipolar primary output at energy $E_{P2}$ and PV delay $PV_2$, each of which may be the same as for the first output or different. For example, the energy $E_{P2}$ may be greater than $E_{P1}$ and the PV delay $PV_2$ may be longer or shorter than $PV_1$. The scenario 1100 also calls for a bipolar back-up pulse using a higher energy $E_{Bi-BU}$. The timing of the back-up pulse may be based in part on a sensing or detecting of an evoked response, for example, if no evoked response is noted in a certain period of time, then a call is made for the back-up pulse. In the scenario 1100, the back-up pulse occurs at a delay of $PV_{Bi-BU}$ due to the lack of an evoked response for the second primary output.

At this point, the scenario 1100 calls for a third primary output using energy $E_{P3}$ and PV delay $PV_3$, which are chosen to maximize capture. Further, detection is switched to unipolar detection per the unipolar detection line 1020. If the unipolar detection fails to detect an evoked response, then it is likely that a problem exists with the bipolar electrode configuration. A back-up unipolar pulse is delivered in this instance at a PV delay of $PV_{U-BU}$ and energy $E_{U-BU}$.

The exemplary scenario 1100 may continue with unipolar primary output with unipolar detection and/or one or more attempts at bipolar detection. Regarding the latter, if an evoked response is detected using a unipolar detection configuration, the detection configuration may be switched to bipolar, a unipolar pulse delivered (e.g., using the same or similar or higher energy output) and then a determination made as to whether bipolar ER detection is faulty as well. In some instances, bipolar output may fail while bipolar ER detection operates, to at least some degree. The reverse situation may also occur. Thus, the various operations performed and associated logic of the exemplary scenario 1100 may help diagnose issues and prevent a pacemaker dependent patient from experiencing any significant period of asystole.

The bipolar primary output and bipolar back-up exhibited in the scenario 1100 can be beneficial for patients that experience significant discomfort with unipolar primary or unipolar back-up pulses. The scenario 1100 only uses unipolar output or back-up when a relatively high energy bipolar output and/or back-up have failed to result in capture. In addition, in the exemplary scenario 1100, lead testing may occur once a relatively high energy bipolar output and/or back-up have failed to result in capture. Lead testing may include impedance and/or other testing.

Figure 12:
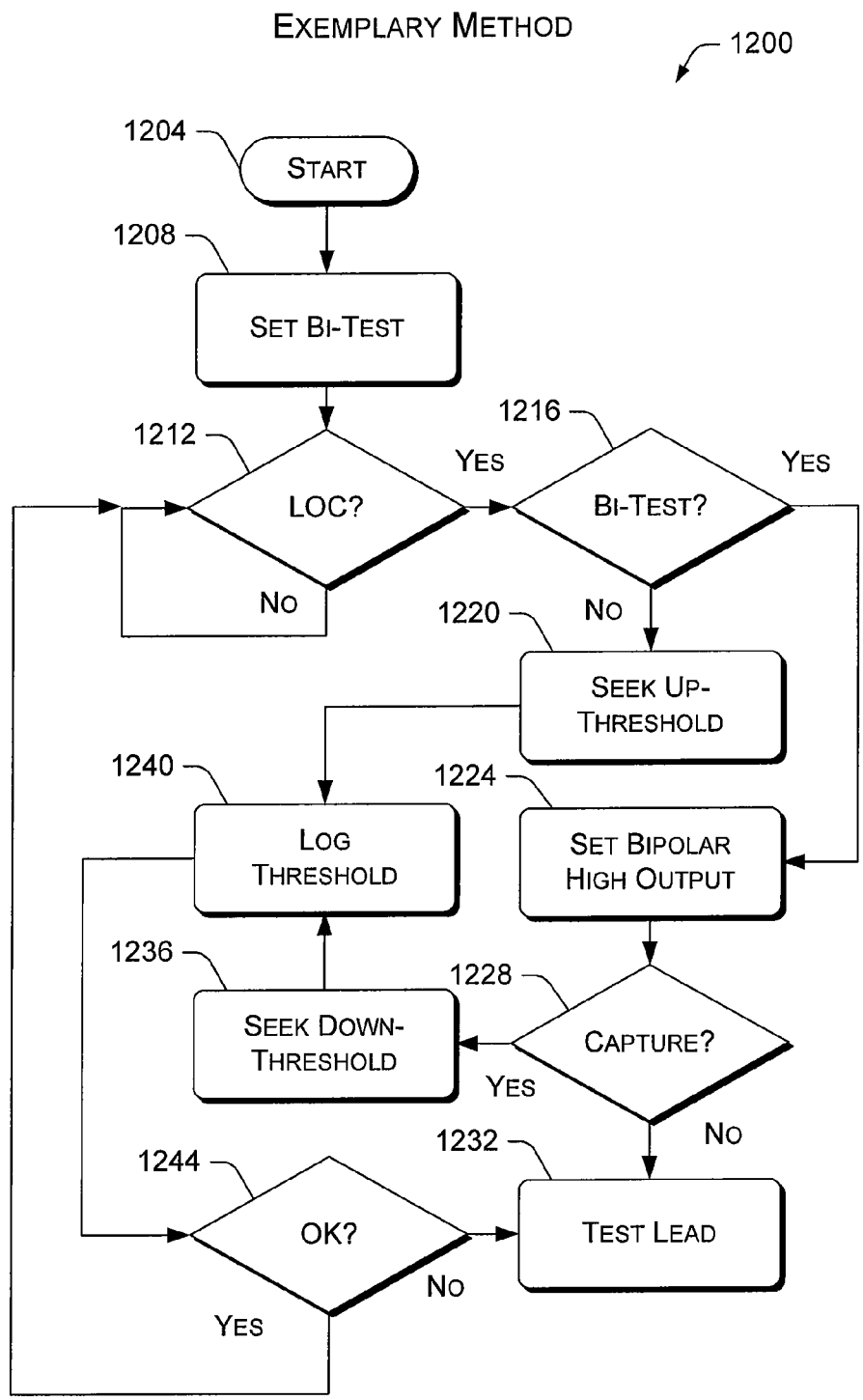
FIG. 12 is a block diagram of an exemplary method that includes a combination of an "up-threshold" search and a "down-threshold" search.

FIG. 12 shows an exemplary method 1200 that includes a bipolar electrode configuration test. The method 1200 commences in a start block 1204 wherein an implantable device is programmed to perform a capture threshold search upon loss of capture. In another example, a capture threshold test may occur at a scheduled time, upon occurrence of an event, etc. In a set block 1208, one or more parameters are set such that a bipolar electrode configuration test occurs in response to a loss of capture if one or more conditions are met. For example, the one or more parameters may call for a bipolar test once out of every ten loss of capture events, once every day if a loss of capture occurs, etc. A care provider may adjust the one or more parameters based in part on information related to patient activity, patient health, lead age, manufacturer information related to a lead, past threshold levels, variation in past threshold levels, etc.

Once the one or more parameters are set, the method 1200 continues in a loss of capture decision block 1212, which relies on detection of the ER signal to decide whether loss of capture has occurred. If loss of capture occurs, then another decision block 1216 follows that decides whether a bipolar electrode configuration test should be run. If the decision block 1216 indicates that such a test is not to be run, then the method 1200 continues in a seek up-threshold block 1220. The seek up-threshold block 1220 performs an algorithm that generally increases output to restore capture. As already mentioned, a periodic threshold test may be performed to lower output if capture threshold has decreased over the period. The result of the up-threshold block 1220 is then stored in a log threshold block 1240. The result is logged optionally with other information, such as, an indication that the result was from an up-threshold search.

If the decision block 1216 decides that a bipolar test should be run, then the method 1200 continues in a set block 1224. The set block 1224 sets a bipolar electrode configuration for output of stimulation that has a relatively high energy level (e.g., about 4 volts or more using the aforementioned AUTOCAPTURE™ algorithm). After delivery of this output stimulation, a decision block 1228 decides if the stimulation resulted in capture. The decision block 1228 may rely on information from one or more sensors. If the decision block 1228 decides that capture did not occur, then the method 1200 continues in a test lead block 1232 that tests the bipolar lead for issues.

If the high output bipolar stimulation resulted in capture, the method 1200 continues in a seek down-threshold block 1236. The seek down-threshold block 1236 performs an algorithm that generally decreases output from a high value capable of achieving capture. The log threshold block 1240 follows the down-threshold block 1236 wherein the threshold is logged, optionally with other information, such as, an indication that the threshold value was obtained using a down-threshold search.

The log threshold block 1240 continues in yet another decision block 1244, which may compare one or more logged thresholds, other information, etc., to decide if a lead test should be performed per the test lead block 1232. If the decision block 1244 decides that the logged information pertaining to threshold is appropriate, then the method 1200 continues in the loss of capture block 1212.

The decision block 1244 may render a decision based on any of a variety of factors. For example, information may be available as to capture hysteresis (e.g., Wedensky effect) that may indicate a lead issue (e.g., stability, integrity, etc.).

As with conventional devices that store capture threshold information, the information logged in the log block 1240 may be available for analysis at a follow-up visit. For example, a care provider may download the information to a computer and make comparisons between the up-threshold and down-threshold results. Such comparisons may allow for better treatment planning and indicate whether a lead issue exists.

Conclusion

Although exemplary mechanisms have been described in language specific to structural features and/or methodological acts, it is to be understood that the subject matter defined in the appended claims is not necessarily limited to the specific features or acts described.

What is claimed is:

1. A method to detect an insulation and/or a conductor defect in a lead, said method comprising:
   delivering a cardiac stimulus using a bipolar electrode configuration at a predetermined energy value associated with a back-up stimulus, wherein the back-up stimulus has in the past produced a depolarization signal having an amplitude sufficient to register an evoked response;

implementing evoked response detection using a unipolar electrode configuration; and if an evoked response did not occur per the detection, then calling for a test of the bipolar electrode configuration.

2. The method of claim 1, further comprising calling for a back-up stimulus using the unipolar electrode configuration if an evoked response did not occur per the detection.

3. The method of claim 1, wherein the delivering does not occur during a myocardial refractory period.

4. The method of claim 1, further comprising delivering another cardiac stimulus using the unipolar electrode configuration, implementing evoked response detection, and if an evoked response did not occur per this detection, then calling for a test of the unipolar electrode configuration.

5. The method of claim 1, wherein the test comprises an impedance test.

6. The method of claim 1, wherein the test provides results that comprise at least one member selected from a group consisting of insulation results and conductor results.

7. A method comprising:

performing an up-threshold search;

performing a down-threshold search that commences with a maximum energy value for a bipolar electrode configuration;

implementing evoked response detection using the bipolar electrode configuration for a stimulus using the maximum energy value; and if an evoked response did not occur per the detection, then performing a lead impedance test for the lead associated with the bipolar electrode configuration.

* * * * *